(12) United States Patent
Oh

(10) Patent No.: US 7,250,162 B2
(45) Date of Patent: Jul. 31, 2007

(54) LACTIC ACID BACTERIA INHIBITING HALITOSIS

(75) Inventor: Jong Suk Oh, Gwangju (KR)

(73) Assignee: Industry Foundation of Chonnam National University, Gwang-Ju (KR)

( * ) Notice: Subject to any disclaimer, the term of this patent is extended or adjusted under 35 U.S.C. 154(b) by 0 days.

(21) Appl. No.: 11/112,833

(22) Filed: Apr. 22, 2005

(65) Prior Publication Data

US 2006/0045870 A1    Mar. 2, 2006

(30) Foreign Application Priority Data

Aug. 25, 2004  (KR) .................... 10-2004-0067109
Mar. 15, 2005  (KR) .................... 10-2005-0021561

(51) Int. Cl.
*A61K 35/74* (2006.01)
*C12N 1/20* (2006.01)

(52) U.S. Cl. ................... 424/93.4; 435/252.1

(58) Field of Classification Search .............. 424/93.4; 435/252.1
See application file for complete search history.

(56) References Cited

U.S. PATENT DOCUMENTS 6,916,647 B1 * 7/2005 Elsser .................... 435/252.1

OTHER PUBLICATIONS

Bjorkroth et al, International Journal of Systematic and Evolutionary Microbiology 2002, vol. 52, p. 141-148.*

* cited by examiner

*Primary Examiner*—Leon B. Lankford, Jr.
*Assistant Examiner*—Laura Schuberg
(74) *Attorney, Agent, or Firm*—Ober/Kaler; Royal W. Craig

(57) ABSTRACT

The present invention relates to novel bacteria inhibiting halitosis or oral malodor. In particular, the present invention relates to novel lactic acid bacteria belonging to the genus *Weissella*, which can inhibit the proliferation of anaerobic bacteria producing volatile sulfur compounds by interacting with them and generating hydrogen peroxide under aerobic and anaerobic conditions. These lactic acid bacteria of the present invention are isolated from lactic acid bacteria naturally existing in the oral cavity of a person, and identified and deposited as *Weissella cibaria* CMU (Accession No.: KCTC 10650BP), *Weissella cibaria* CMS-1 (Accession No.: KCTC 10678BP), *Weissella cibaria* CMS-2 (Accession No.: KCTC 10679BP) and *Weissella cibaria* CMS-3 (Accession No.: KCTC 10680BP), respectively. The present invention provides the lactic acid bacteria and foods comprising the same for effectively inhibiting the proliferation of halitosis-inducing anaerobic bacteria without corrosion at teeth by using these *Weissella cibaria* lactic acid bacteria strains.

3 Claims, No Drawings

LACTIC ACID BACTERIA INHIBITING HALITOSIS

CROSS-REFERENCE TO RELATED APPLICATIONS

The present application derives priority from Korean Patent Application No. 2004-0067109 filed on Aug. 25, 2004, and No. 2005-0021561 filed on Mar. 15, 2005.

BACKGROUND OF THE INVENTION

1. Field of the Invention

The present invention relates to novel bacteria inhibiting halitosis or oral malodor emanating from the oral cavity. More specifically, the present invention relates to novel lactic acid bacteria that are isolated among microorganisms normally existing in the oral cavity of a person. These lactic acid bacteria are novel lactic acid bacteria belonging to genus *Weissella* that inhibit the proliferation of anaerobic bacteria producing volatile sulfur compounds by interacting with them and producing hydrogen peroxide under aerobic and anaerobic conditions.

2. Description of the Background

Halitosis or oral malodor is bad breath derived from the oral cavity and organs adjacent thereto, and many people suffer from halitosis in everyday life. About 85 to 90% of halitosis is originated from the oral cavity, especially, a rear part of the tongue. Major components of halitosis are volatile sulfur compounds, and about 90% of the total volatile sulfur compounds consist of hydrogen sulfide made from cysteine and methyl mercaptan made from methionine. These compounds are produced by anaerobic bacteria, and the rear part of the tongue is the most important inhabitation for the anaerobic bacteria. Since it is impossible to completely clean this part with saliva and there are many small crevices, the anaerobic bacteria can continuously survive in the rear part of the tongue. Although the production of volatile sulfur compounds by anaerobic bacteria is a major cause of halitosis, halitosis may also be caused by oral diseases such as tooth decay and periodontitis. Bacteria that produce hydrogen sulfide from cysteine include genus *Peptostreptococcus*, genus *Eubacterium*, genus *Selenomonas*, genus *Centipeda*, genus *Bacteroides* and genus *Fusobacterium*; and bacteria that produce methyl mercaptan from methionine include genus *Fusobacterium*, genus *Bacteroides*, genus *Porphyromonas* and genus *Eubacterium*. Especially, *Fusobacterium nucleatum*, *Prevotella intermedia* and *Porphyromonas gingivalis* are frequently found in the oral cavity of a halitosis patient. Genus *Bacteroides*, genus *Porphyromonas* and genus *Prevotella* are too similar to one another to such an extent that they have been previously known as belonging to the same genus. Many kinds of anaerobic bacteria are responsible for halitosis, but the representative bacteria for the development of halitosis are *Fusobacterium nucleatum* and *Porphyromonas gingivalis*.

Since the most effective way to prevent halitosis is to inhibit the proliferation of anaerobic bacteria producing volatile sulfur compounds known as major components of halitosis, a method for removing tongue fur with a tongue scraper to eliminate substrates for the bacterial proliferation from the tongue, or for treating the tongue with a metal salt such as zinc chloride or a disinfectant such as alcohol or chlorhexidine to inhibit the production of volatile sulfur compounds by anaerobic bacteria has been previously employed. However, there are problems in that the metal salt and disinfectant inhibit the growth of other harmless oral microorganisms as well as halitosis-inducing anaerobic bacteria. Since they are not swallowed into the gullet, they do not reach a rear part of the tongue that is a place of concern in the development of halitosis. They are merely gargled in a front part of the oral cavity and then spat out of the mouth. Thus, there is a problem in that they cannot clean the rear part of the tongue which is the main place for the proliferation of halitosis-inducing anaerobic bacteria. Further, since they are diluted with saliva and swallowed into the gullet together with the saliva, their cleansing effects in the oral cavity last only for 20 minutes to 2 hours. Thereafter, anaerobic bacteria proliferate again in the oral cavity, thereby inducing halitosis again. Therefore, the metal salt and disinfectant used for decreasing halitosis are effective only in a short period of time.

Recently, there has been an attempt to inhibit the proliferation of anaerobic bacteria using lactic acid bacteria in vitro. The lactic acid bacteria are bacteria producing lactic acid as a final product by fermenting a carbohydrate, exist in the oral cavities and digestive tracts of a person and an animal, and are typically used for manufacturing a fermented food such as Kimchi or yogurt. The lactic acid bacteria used for the food industry include genus *Enterococcus*, genus *Lactobacillus*, genus *Lactococcus*, genus *Leuconostoc*, genus *Streptococcus* and genus *Weissella*. However, since these lactic acid bacteria are diluted with saliva and directly swallowed into the gullet when orally administered, there is a problem in that they are difficult to remain in the oral cavity. Further, lactic acid bacteria such as *Lactobacillus acidophilus*, *Lactobacillus casei* and *Lactobacillus salivarius* can inhibit the in vitro proliferation of anaerobic bacteria by producing a strong acid, but this strong acid produced by the lactic acid bacteria is neutralized by the buffering function of saliva in the oral cavity of a healthy person. Accordingly, it is hard to inhibit the bacterial proliferation. Furthermore, since the strong acid causes dental caries, the continuous administration of these bacteria may give rise to problems in oral hygiene.

SUMMARY OF THE INVENTION

To overcome these problems, the present inventors have endeavored to settle lactic acid bacteria, which can inhibit the proliferation of halitosis-inducing anaerobic bacteria, in the oral cavity. The present invention intends to prepare lactic acid bacteria that produce hydrogen peroxide under aerobic and anaerobic conditions by interacting with anaerobic bacteria producing volatile sulfur compounds.

Heretofore, it has been believed that if lactic acid bacteria stay long in the oral cavity, they produce lactic acid and cause dental corrosion. That is, their function has been determined to be negative. However, since the lactic acid bacteria of the present invention produce a small quantity of lactic acid and do not increase oral acidity, they inhibit the proliferation of halitosis-inducing anaerobic bacteria without corrosion at teeth, which results in effectively preventing the development of halitosis. Therefore, an object of the present invention is to provide novel lactic acid bacteria that inhibit the proliferation of halitosis-inducing anaerobic bacteria through a mechanism completely different from a metal salt or a disinfectant. Further, another object of the present invention is to provide a lactic acid bacterial formulation as a food comprising the lactic acid bacteria for inhibiting the proliferation of halitosis-inducing anaerobic bacteria, so that the lactic acid bacterial formulation can be drunk or eaten. Since the formulation passes through a rear part of the oral cavity when drunken or eaten, it can settle on a rear part of the tongue and allow the proliferation of the lactic acid bacteria, thereby effectively inhibiting the proliferation of anaerobic bacteria.

DETAILED DESCRIPTION OF THE INVENTION

The present invention is conceived to achieve these objects and is directed to lactic acid bacteria identified as *Weissella cibaria* that show a negative signal in the catalase production, grow at a temperature range of 25 to 42° C., and produce hydrogen peroxide under aerobic and anaerobic conditions by interacting with anaerobic bacteria producing volatile sulfur compounds.

Specifically, the *Weissella cibaria* lactic acid bacteria according to the present invention are characterized in that due to their low productivity in lactic acid, their acidity is not high enough to cause corrosion at teeth, and in that they interact with halitosis-inducing anaerobic bacteria. Further, the present invention relates to a lactic acid bacterium belong to genus *Weissella*, *Weissella cibaria* CMU KCTC 10650BP, which can interact with the halitosis-inducing anaerobic bacteria and produce hydrogen peroxide under aerobic and anaerobic conditions. Furthermore, other *Weissella cibaria* lactic acid bacteria according to the present invention include *Weissella cibaria* CMS-1 KCTC 10678BP, *Weissella cibaria* CMS-2 KCTC 10679BP or *Weissella cibaria* CMS-3 KCTC 10680BP.

According to another aspect of the present invention, there is provided a food in the form of a drinkable or eatable lactic acid bacterial formulation prepared using the *Weissella cibaria* lactic acid bacteria alone or a mixture thereof to inhibit the proliferation of anaerobic bacteria producing volatile sulfur compounds. Since the lactic acid bacteria of the food pass through a rear part of the oral cavity, they can settle and proliferate on a rear part of the tongue, thereby effectively inhibiting the proliferation of anaerobic bacteria.

Further, according to a further aspect of the present invention, there is provided a method for examining whether the *Weissella cibaria* lactic acid bacteria interact with the halitosis-inducing anaerobic bacteria and produce hydrogen peroxide, and isolating and identifying the lactic acid bacteria inhibiting halitosis. The method comprises the steps of culturing a lactic acid bacterial sample in a MRS medium for 1 day, centrifuging the culture solution at 6,000 rpm and 4° C. for 10 minutes to separate a cell pellet, washing the cell pellet with 0.85% saline once, and suspending it in a buffer; adding 1 ml of each of the suspension to a test tube, mixing them for 10 seconds, shaking the mixture at 37° C. and 110 rpm for 30 minutes, and keeping it at room temperature for 3 minutes; selecting samples of lactic acid bacteria showing a transparent supernatant among the test tubes; inoculating 3 μl of each of the selected samples in a medium prepared by adding 0.25 mg/ml of 3,3',5,5'-tetramethylbenzidine and 0.01 mg/ml of peroxidase to a MRS solid medium, and examining whether they form a blue colony in order to isolate a strain producing hydrogen peroxide from the selected samples; isolating a lactic acid bacteria strain producing the hydrogen peroxide under aerobic and anaerobic conditions; and identifying the isolated lactic acid bacteria strain with 16S rRNA sequencing analysis.

From the results of tests performed by sampling and isolating lactic acid bacteria naturally existing in the oral cavity of a person and examining their inhibitory effects on the proliferation of anaerobic bacteria in vitro and in vivo, the inventors found that the *Weissella cibaria* lactic acid bacteria significantly inhibit the development of halitosis.

The isolated strains inhibiting halitosis according to the present invention were designated *Weissella cibaria* CMU, *Weissella cibaria* CMS-1, *Weissella cibaria* CMS-2 and *Weissella cibaria* CMS-3, and deposited on Jun. 4 and Aug. 6, 2004 in the Biological Resources Center of the Korea Research Institute of Bioscience and Biotechnology at the following address: #52 Oun-dong, Yusung-ku, Taejon 305-303, Republic of Korea, with the accession numbers KCTC 10650BP, KCTC 10678BP, KCTC 10679BP and KCTC 10680BP, respectively.

Since the lactic acid bacteria of the present invention can immediately interact with the representative halitosis-inducing anaerobic bacteria such as *Fusobacterium nucleatum* or *Phorphyromonas gingivalis*, when the lactic acid bacteria of the present invention are orally administered, they interact with the anaerobic bacteria such as *Fusobacterium nucleatum* or *Phorphyromonas gingivalis*, produce hydrogen peroxide under an anaerobic condition as well as an aerobic condition, and consequently, inhibit the proliferation of the anaerobic bacteria with which they have interacted. Especially, since the anaerobic bacteria proliferate and exert their metabolic activity under an anaerobic condition, the production of hydrogen peroxide by the lactic acid bacteria under anaerobic condition is important to inhibit the proliferation of the anaerobic bacteria.

The lactic acid bacteria of the present invention show the morphological and physiological properties as follows. The lactic acid bacteria strains inhibiting halitosis according to the present invention, i.e., *Weissella cibaria* CMU, *Weissella cibaria* CMS-1, *Weissella cibaria* CMS-2 and *Weissella cibaria* CMS-3, belong to the genus *Weissella*, can proliferate in a MRS medium, and are identified as Gram-positive bacilli. They show negative signals in catalase production, can grow at 25° C., 35° C. and 42° C., interact with the anaerobic bacteria responsible for the production of volatile sulfur compounds, produce hydrogen peroxide under aerobic and anaerobic conditions, and finally, form a blue colony. The lactic acid bacteria of the present invention have ability to degrade carbohydrates such as L-arabinose, amygdalin, cellobiose, esculin, fructose, galactose, gentiobiose, gluconate, N-acetyl-glucosamine, glucose, maltose, mannose, salicin, sucrose and D-xylose.

As described above, the present invention composes of the process of isolating and identifying novel lactic acid bacteria inhibiting halitosis and the process of applying the novel lactic acid bacteria to clinical experiments. Hereinafter, the lactic acid bacteria inhibiting halitosis according to the present invention will be described in detail in connection with the following Examples and Application Examples. The present invention can be better understood from the following Examples, and the following Examples are only for illustrative purposes and are not intended to limit the scope of the present invention defined by appended claims.

EXAMPLE 1

Isolation and Identification of Lactic Acid Bacteria According to the Present Invention First, the inventors collected 3,000 strains of lactic acid bacterial samples from the oral cavity of a person. To examine their binding affinity to an anaerobic bacterium, *Fusobacterium nucleatum*, the lactic acid bacterial samples were cultured in a MRS medium for 1 day, and *Fusobacterium nucleatum* ATCC 10953 was cultured in a brain heart infusion medium supplemented with 1% yeast extract, 5

μg/ml of hemin, 1 μg/ml of vitamin $K_1$ for 1 day. The culture solutions were centrifuged at 6,000 rpm and 4° C. for 10 minute to separate cell pellets, respectively, and the cell pellets were then washed with 0.85% saline and suspended in a buffer. Then, 1 ml of each of the suspensions was added to a test tube, mixed for 10 seconds, shaken at 110 rpm and 37° C. for 30 minutes, and kept at room temperature for 3 minutes. Among the examined lactic acid bacteria, lactic acid bacteria showing a transparent supernatant were selected. To isolate a strain producing hydrogen peroxide from the selected lactic acid bacteria, 3 μl of each of the lactic acid bacterial culture solutions was inoculated into a MRS medium supplemented with 0.25 mg/ml of 3,3',5,5'-tetramethylbenzidine and 0.01 mg/ml of peroxidase, and it was observed whether a blue colony was formed. Next, four lactic acid bacteria strains capable of immediately interacting with *Fusobacterium nucleatum* and producing hydrogen peroxide under aerobic and anaerobic conditions were isolated therefrom. The isolated four lactic acid bacteria strains were identified with 16S rRNA sequencing analysis. As a result, it has been found that all the four lactic acid bacteria strains were identified as *Weissella cibaria*.

EXAMPLE 2

Comparison Tests of Binding Affinities and Hydrogen Peroxide Production

Between the Lactic Acid Bacteria of the Present Invention and Standard Lactic Acid Bacteria with Respect to Anaerobic Bacteria Producing Volatile Sulfur Compounds Binding affinities of standard lactic acid bacteria and the four lactic acid bacteria strains isolated and identified in Example 1 according to the present invention to *Fusobacterium nucleatum* and *Porphyromonas gingivalis* A7A1-28 known as major anaerobic bacteria producing volatile sulfur compounds in the oral cavity were examined through tests as follows. At this time, *Enterococcus faecalis* (ATCC 29212), *Lactobacillus casei* (ATCC 334), *Lactobacillus acidophilus* (ATCC 4356), *Lactobacillus fermentum* (ATCC 14931), *Lactobacillus salivarius* (ATCC 11742), *Streptococcus oralis* (ATCC 35037), *Streptococcus salivarius, Weissella confusa* (ATCC 10881), *Weissella kimchi* CHJ3 and *Weissella cibaria* CCUG41967 were employed as the standard lactic acid bacteria. First, *Fusobacterium nucleatum* was cultured in a brain heart infusion medium supplemented with 1% yeast extract, 5 μg/ml of hemin and 1 μg/ml of vitamin $K_1$ for 1 day; *Porphyromonas gingivalis* was cultured in a brain heart infusion medium supplemented with 0.5% yeast extract, 5 μg/ml of hemin and 1 μg/ml of vitamin $K_1$ for 2 days; and the lactic acid bacteria were cultured in a MRS medium or a brain heart infusion medium for 1 day. The culture solutions were centrifuged at 6,000 rpm and 4° C. for 10 minutes to separate cell pellets, respectively. Each of the cell pellets was washed with saline once and suspended in a buffer (0.021 M $Na_2HPO_4/NaH_2PO_4$, 36 mM NaCl, 0.96 mM $CaCl_2$, pH 7.3) having a composition similar to that of saliva. 1 ml of each of the lactic acid bacterial suspensions and the anaerobic bacterial suspension thus prepared was added to a test tube alone or in combination therewith, mixed for 10 seconds, shaken at 110 rpm and 37° C. for 30 minutes, and then, kept at room temperature for 3 minutes.

Here, 0.5 ml of a supernatant was taken from each of the mixtures before and after the shaking for 30 minutes, and its optical density (OD; absorbance) was measured with a spectrophotometer at a wavelength of 660 nm. To examine whether hydrogen peroxide is produced under anaerobic and aerobic conditions, 3 μg/ml of each of the lactic acid bacterial culture solutions was inoculated into a medium supplemented with 3,3',5,5'-tetramethylbenzidin and peroxidase and the formation of a blue colony was examined.

Table 1 below shows the comparison test results of binding affinities and hydrogen peroxide production between the lactic acid bacteria of the present invention and 10 standard lactic acid bacteria with respect to anaerobic bacteria producing volatile sulfur compounds.

TABLE 1

| | OD when bound with FN* | | OD when bound with PG** | | Hydrogen peroxide production | |
|---|---|---|---|---|---|---|
| | | | | | Anaerobic | Aerobic |
| Lactic acid bacteria | 0 min | 30 min | 0 min | 30 min | condition | condition |
| *Enterococcus faecalis* | 1.238 | 0.707 | 0.963 | 0.485 | − | − |
| *Lactobacillus casei* | 1.883 | 1.103 | 1.857 | 0.681 | − | − |
| *Lactobacillus acidophilus* | 1.829 | 1.485 | 1.713 | 1.368 | − | − |
| *Lactobacillus fermentum* | 1.717 | 1.608 | 1.565 | 1.233 | − | − |
| *Lactobacillus salivarius* | 1.974 | 0.547 | 2.028 | 1.430 | − | + |
| *Streptococcus oralis* | 1.340 | 0.489 | 1.441 | 1.176 | − | + |
| *Streptococcus salivarius* | 1.531 | 0.192 | 1.608 | 0.238 | − | − |
| *Weissella confusa* | 1.824 | 1.017 | 1.532 | 1.338 | − | − |
| *Weissella kimchi* | 1.817 | 1.652 | 1.689 | 1.434 | − | + |
| *Weissella cibaria* CCUG 41967 | 1.790 | 1.517 | 1.680 | 1.368 | + | + |
| *Weissella cibaria* CMU | 1.854 | 0.363 | 1.783 | 0.067 | + | + |
| *Weissella cibaria* CMS-1 | 1.861 | 0.382 | 1.731 | 0.808 | + | + |
| *Weissella cibaria* CMS-2 | 1.864 | 0.308 | 1.781 | 0.154 | + | + |
| *Weissella cibaria* CMS-3 | 1.871 | 0.418 | 1.707 | 0.725 | + | + |

*FN *Fusobacterium nucleatum*
**PG *Porphyromonas gingivalis*

As can be seen in Table 1, it was found from the tests of the binding affinity and hydrogen peroxide production of the lactic acid bacteria with respect to anaerobic bacteria that all the standard lactic acid bacteria did not produce hydrogen peroxide under an anaerobic condition, whereas only the *Weissella cibaria* strains produced hydrogen peroxide under both aerobic and anaerobic conditions. However, *Weissella cibaria* CCUG 41967 that is a *Weissella cibaria* standard strain showed lower binding affinities to *Fusobacterium nucleatum* and *Porphyromonas gingivalis* than that of the lactic acid bacteria of the present invention, and thus, the optical densities of supernatants thereof after the shaking for 30 minutes were 1.517 and 1.368 that are relatively high. In case of combining the lactic acid bacteria of the present invention with *Fusobacterium nucleatum*, the optical densities of the supernatants before the shaking were 1.854, 1.861, 1.864 and 1.871, and they decreased to 0.363, 0.382, 0.308 and 0.418 after the shaking for 30 minutes, respectively. In case of combining the lactic acid bacteria of the present invention with *Porphyromonas gingivalis*, the optical densities of the supernatants before the shaking were 1.783, 1.731, 1.781 and 1.707, and they decreased to 0.067, 0.808, 0.154 and 0.725 after the shaking for 30 minutes, respectively. That is, *Weissella cibaria* CCUG 41967 that is a *Weissella cibaria* standard strain showed the optical densities different from the four lactic acid bacteria strains of the present invention. From these results, it can be understood that only the four lactic acid bacteria strains of the present invention produce hydrogen peroxide under both aerobic and anaerobic conditions and interact well with the major anaerobic bacteria producing volatile sulfur compounds.

EXAMPLE 3

Comparison Tests of Inhibitory Effects on the Development of Halitosis in the Oral Cavity Between the Lactic Acid Bacteria of the Present Invention and Standard Lactic Acid Bacteria To confirm clinical, inhibitory effects on the development of halitosis between the lactic acid bacteria of the present invention and the standard lactic acid bacteria described in Example 2, the concentration of volatile sulfur compounds, especially hydrogen sulfide, methyl mercaptan and dimethyl sulfide, in the oral cavity of a person was measured with Oralchroma® (Tagasago, Japan). The concentration of volatile sulfur compounds in the oral cavity of each of persons may significantly vary according to several factors, e.g., the presence or absence of gargling, time when a meal is taken, the time of day, and stress. However, it usually show a constant value at dawn, and thus, this value was regarded as a control. First, each of the subjects got up in the morning ordinarily, did not take any food or beverage and did not brush their teeth. Under these conditions, the concentration of volatile sulfur compounds in the oral cavity was measured with Oralchroma® once a day for three days, and the average was calculated from the measured values and then regarded as a control. To examine inhibitory effects of the lactic acid bacteria on the production of oral volatile sulfur compounds, at the time when 30 minutes after having lunch and dinner and brushing teeth passed, the subject gargled with a lactic acid bacterial suspension, which was prepared by suspending lactic acid bacteria in 15 ml of distilled water at an amount of $1 \times 10^9$ cells, for 1 minute, held the suspension in his/her mouth for 1 minute, and then, swallowed. In the morning of the next day, the subject did not take any food or beverage and brush his/her teeth, and the concentration of oral volatile sulfur compounds was repeatedly measured with Oralchroma® three times. In the same manner as the previous day, at the time when 30 minutes after having lunch and dinner and brushing teeth passed, the subject gargled with the lactic acid bacterial suspension, which was prepared by suspending $1 \times 10^9$ cells of the isolated strain in 15 ml of distilled water, for 1 minute, held the suspension in his/her mouth for 1 minute, and then, swallowed. In the morning of the next day, the subject did not take any food or beverage and brush his/her teeth, and the concentration of oral volatile sulfur compounds was repeatedly measured with Oralchroma® three times.

Table 2 below shows inhibitory effects on the development of halitosis when the lactic acid bacteria of the present invention were orally administered.

TABLE 2

| | Percentage of inhibiting halitosis (the number of subjects showing decreased halitosis/the total number of subects) | | |
|---|---|---|---|
| Administered strains | First day after administration | Second day after administration | Sum |
| *Weissella cibaria* CMU | 52.9% (37/70) | 17.1% (12/70) | 70.0% (49/70) |
| *Weissella cibaria* CMS-1 | 54.5% (6/11) | 18.2% (2/11) | 72.7% (8/11) |
| *Weissella cibaria* CMS-2 | 50.0% (5/10) | 10.0% (1/10) | 60.0% (6/10) |
| *Weissella cibaria* CMS-3 | 40.0% (4/10) | 30.0% (3/10) | 70.0% (7/10) |

As shown in Table 2, among 70 subjects that drank *Weissella cibaria* CMU, 37 subjects (52.9%) showed the concentration of volatile sulfur compounds decreased by 50% or more within a day as compared with the control, and 12 subjects (17.1%) showed the concentration of volatile sulfur compounds decreased by 50% or more within two days. Thus, the total number of subjects showing the concentration of volatile sulfur compounds decreased by 50% or more within two days was 49 (70.0%), and 21 subjects (30.0%) did not show any decreased concentration. 8 subjects (72.7%) out of 11 subjects that drank *Weissella cibaria* CMS-1, 6 subjects (60.0%) out of 10 subjects that drank CMS-2, and 7 subjects (70.0%) out of 10 subjects that drank *Weissella cibaria* CMS-3 showed the concentration of volatile sulfur compounds decreased by 50% or more as compared with the control. Especially, among 11 subjects having severe halitosis who showed over 1,000 ppb of the concentration of volatile sulfur compounds when measured with Oralchroma®, 8 subjects showed the concentration thereof decreased by 50% or more within a day after drinking *Weissella cibaria* CMU, and 2 subjects showed the concentration thereof decreased by 50% or more within two days. Thus, the total number of subjects showing decreased concentration was 10 (90.9%). These results suggest that the lactic acid bacteria of the present invention are more effective for a person having severe halitosis. However, as a result of testing the standard lactic acid bacteria strains for three subjects, there were no inhibitory effects of all the standard lactic acid bacteria strains on the development of halitosis. Therefore, it was confirmed that only the four lactic acid bacteria strains of the present invention clinically exhibited high inhibitory effects on the development of halitosis.

Next, application examples of halitosis-inhibiting formulations manufactured by applying the novel lactic acid bacteria of the present invention to foods will be described.

APPLICATION EXAMPLE 1

Yogurt Goods

By making a request to a yogurt manufacturer, a yogurt test sample was prepared by adding 0.1 volume % of a culture solution of the lactic acid bacteria of the present invention to a conventional fermentative strain just prior to fermentation, and mixing and fermenting the mixture. 10 panelists sampled the prepared yogurt test sample. As a result, they answered that there was no difference in flavor between the test sample and a control (the existing yogurt). Further, an experimental group was prepared by adding 0.2 volume % of the lactic acid bacteria of the present invention before sealing in the process of manufacturing yogurt and by being then sealed, and a control group was prepared without adding the lactic acid bacteria of the present invention. When 10 panelists sampled the experimental and control groups, they answered that there was no difference in flavor between them.

APPLICATION EXAMPLE 2

Kimchi Goods

Five heads of cabbage were sliced with a thickness of 4 to 5 cm, salted, washed and dehydrated. The salted cabbage was seasoned with spices and matured at 20° C. for 3 days. An experimental group was prepared by mixing the naturally matured cabbage with 0.2 weight % of a lactic acid bacterial culture solution of the present invention, and a control group was prepared without adding the lactic acid bacterial culture solution. The experimental and control groups were served at table and sampled by 10 panelists. As a result, they answered that there was no difference in Kimchi flavor between the experimental and control groups.

APPLICATION EXAMPLE 3

Butter Goods

The freeze-dried lactic acid bacteria strain of the present invention were mixed with a butter composition manufactured by means of a conventional method at an amount of 0.2 weight % before packing into a butter test sample. When 10 panelists sampled the butter goods thus prepared, they answered that there was no difference in butter flavor.

APPLICATION EXAMPLE 4

Gum Goods

The freeze-dried lactic acid bacteria strain of the present invention were mixed with a gum composition manufactured by means of a conventional method at an amount of 0.2 weight % before packing into gum goods. When 10 panelists sampled the gum goods thus prepared, they answered that there was no difference in gum flavor.

As described above, when a person takes novel foods or beverages using the lactic acid bacteria of the present invention, the lactic acid bacteria produce hydrogen peroxide by interacting with anaerobic bacteria, inhibit the production of volatile sulfur compounds, and finally, prevent the development of halitosis.

The present invention can be applied, but is not limited to, to any foods such as cheese, shortening, ice cream and margarine in addition to the foods disclosed herein.

Further, test for safety of the halitosis-inhibiting lactic acid bacteria according to the present invention, *Weissella cibaria* CMU (KCTC 10650BP), *Weissella cibaria* CMS-1 (KCTC 10678BP), *Weissella cibaria* CMS-2 (KCTC 10679BP) and *Weissella cibaria* CMS-3 (KCTC 10680BP), were conducted as follows.

Tests for Safety of the Halitosis-inhibiting Lactic Acid Bacteria

The safety of the halitosis-inhibiting lactic acid bacteria according to the present invention was examined. First, isolated strains were inoculated into a blood agar medium and cultured at 37° C. for 24 hours. As a result, all the isolated strains did not show any β-lysis. Even when each of the isolated strains was inoculated into a gelatin medium and cultured at 35° C. for 6 weeks, gelatin was not liquefied.

Next, it was examined whether the lactic acid bacteria of the present invention produce harmful metabolites. To confirm whether they produce ammonia, each of the isolated strains was inoculated into a urea agar medium and cultured at 37° C. for 12 hours. As a result, there was no color change in all the culture media, indicating negative. To examine whether they produce indole, each of the isolated strains was inoculated into a tryptophan medium and cultured at 37° C. for 18 hours, and 5 drops of a Kovac's reagent were added thereto. As a result, all the isolated strains showed negative signals with no color change in the culture medium. To examine whether they produce phenylpyruvic acid from phenylalanine by way of deamination, each of the isolated strains was inoculated into a phenylalanine agar medium and cultured at 37° C. for 24 hours and 5 drops of a 10% ferric chloride solution were added thereto. As a result, there was no color change in all the culture media, indicating negative.

Subsequently, it was examined whether the isolated strains produce harmful enzymes, as follows. To confirm whether β-glucuronidase is produced, after ρ-nitrophenyl-β-D-glucuronide was dissolved in 0.1 M sodium phosphate buffer (pH 6.0) at a final concentration of 0.2%, this solution was mixed with a suspension of each of the isolated strains at an identical volume and reacted at 37° C. for 16 hours. As a result, all the isolated strain culture solutions did not change into yellow, indicating negative. To examine whether they produce 7α-dehydroxylase, after cholic acid and chenodeoxycholic acid were dissolved in 0.1 M sodium phosphate buffer at a final concentration of 0.016%, this solution was mixed with the suspension of each of the isolated strains and reacted at 37° C. for 30 minutes. 3 drops of 6 N hydrochloric acid solution was added to the mixture to stop enzyme reaction. Thereafter, the mixture was extracted with ethyl acetate three times, dried with nitrogen gas, and subjected to thin-layer chromatography (TLC). The TLC was conducted through the steps of putting 20 μl of a sample on the bottom of a TLC plate and drying it, developing with a developing agent, drying it at 40° C. for 10 minutes, spraying 50% sulfuric acid thereon and keeping it at 180° C. for 2 minutes. As a result, there was no conversion of cholic acid into deoxycholic acid and chenodeoxycholic acid into lithocholic acid in all the isolated strains. To confirm whether nitroreductase is produced, 4-nitrobenzoic acid and trichloroacetic acid were added to a supernatant of each of homogenized isolated strains and reacted at 37° C. for 1 hour, which showed that all the isolated strains were negative with no color change into red. To examine platelet aggregation, each of the isolated strains and a triggering agent for platelet aggregation, ADP, were added to a serum including a large quantity of platelet, and the degree of platelet aggregation was measured. As a result, all the isolated strains showed negative for platelet aggregation.

As described above, in the safety tests for examining whether the halitosis-inhibiting lactic acid bacteria according to the present invention produce harmful metabolites and enzymes, it was confirmed that they show negative signals in all the tests, which suggests that they are safe.

Therefore, since the novel lactic acid bacteria of the present invention confirmed through the tests for examining interaction thereof with anaerobic bacteria producing volatile sulfur compounds and the effects thereof on inhibition of halitosis in the oral cavity have the inhibitory effects on the development of halitosis, they can be effectively used in the dentistry industry. The present invention provides the lactic acid bacteria that produce hydrogen peroxide by interacting with the anaerobic bacteria under aerobic and anaerobic conditions and permit the lactic acid bacteria capable of inhibiting the proliferation of halitosis-inducing anaerobic bacteria to be settled in the oral cavity.

Since the lactic acid bacteria of the present invention produce a small quantity of lactic acid and do not increase acidity, they inhibit the proliferation of halitosis-inducing anaerobic bacteria without corrosion at teeth, which results in effective prevention of the development of halitosis. Further, when the lactic acid bacteria of the present invention are drunk or eaten by applying them to foods, they pass through a rear part of the oral cavity and they can settle and proliferate in a rear part of the tongue, thereby inhibiting the proliferation of anaerobic bacteria. Accordingly, they can be effectively used for the food industry and heath/medical industry.

What is claimed is:

1. A biologically pure culture of a *Weissella cibaria* lactic acid bacteria strain, the lactic acid bacteria strain showing negative in catalase production, growing at a temperature range of 25° C. to 42° C., and producing hydrogen peroxide under aerobic and anaerobic conditions by interacting with anaerobic bacteria producing volatile sulfur compounds, wherein the *Weissella cibaria* lactic acid bacteria strain is *Weissella cibaria* CMU (KCTC 10650BP), *Weissella cibaria* CMS-1 (KCTC 10678BP), *Weissella cibaria* CMS-2 (KCTC 10679BP) or *Weissella cibaria* CMS-3 (KCTC 10680BP).

2. A food in the form of a drinkable or eatable lactic acid bacterial formulation prepared using the *Weissella cibaria* lactic acid bacteria strain according to claim 1, so that the lactic acid bacteria of the food pass through a rear part of the oral cavity and can settle and proliferate on a rear part of the tongue, thereby effectively inhibiting the proliferation of the anaerobic bacteria.

3. A method for isolating and identifying the *Weissella cibaria* lactic acid bacteria strain according to claim 1, comprising the steps of:

culturing a lactic acid bacterial sample in a MRS medium for 1 day, centrifuging the culture solution at 6,000 rpm and 4° C. for 10 minutes to separate a cell pellet, washing the cell pellet with 0.85% saline once, and suspending it in a buffer;

adding 1 ml of each of the suspension to a test tube, mixing them for 10 seconds, shaking the mixture at 37° C. and 110 rpm for 30 minutes, and keeping it at room temperature for 3 minutes;

selecting samples of lactic acid bacteria showing a transparent supernatant among the test tubes;

inoculating 3 ul of each of the selected samples in a medium prepared by adding 0.25 mg/ml of 3,3',5,5'-tetramethylbenzidine and 0.01 mg/ml of peroxidase to a MRS solid medium, and examining whether they form a blue colony in order to isolate a strain producing hydrogen peroxide from the selected samples;

isolating a lactic acid bacteria strain producing the hydrogen peroxide under aerobic and anaerobic conditions; and identifying the isolated lactic acid bacteria strain with 16S rRNA sequencing analysis.

* * * * *